US012766340B2

(12) United States Patent
Tang et al.

(10) Patent No.: US 12,766,340 B2
(45) Date of Patent: Oct. 20, 2026

(54) METHOD AND DEVICE FOR DETERMINING RADIATION DELIVERY PLAN, AND COMPUTER EQUIPMENT

(71) Applicant: Shanghai United Imaging Healthcare Co., Ltd., Shanghai (CN)

(72) Inventors: Junxiang Tang, Shanghai (CN); Kang Zhang, Shanghai (CN); Jingjie Zhou, Shanghai (CN)

(73) Assignee: Shanghai United Imaging Healthcare Co., Ltd., Shanghai (CN)

( * ) Notice: Subject to any disclaimer, the term of this patent is extended or adjusted under 35 U.S.C. 154(b) by 130 days.

(21) Appl. No.: 18/808,120

(22) Filed: Aug. 19, 2024

(65) Prior Publication Data

US 2025/0058147 A1 Feb. 20, 2025

(30) Foreign Application Priority Data

Aug. 17, 2023 (CN) ........................ 202311044767.X

(51) Int. Cl.
*A61N 5/10* (2006.01)

(52) U.S. Cl.
CPC .................................. *A61N 5/1031* (2013.01)

(58) Field of Classification Search
CPC .......... A61N 5/1031; A61N 2005/1041; A61N 5/1039; G16H 20/40
See application file for complete search history.

(56) References Cited

U.S. PATENT DOCUMENTS

2014/0350863 A1* 11/2014 Hartman ............. A61N 5/1031 702/19

FOREIGN PATENT DOCUMENTS

CN 111145866 A 5/2020

* cited by examiner

*Primary Examiner* — Kiho Kim

(57) ABSTRACT

A method and a device for determining a radiation delivery plan, a computer equipment, a storage medium and a computer program product. The method includes: obtaining an image of a target object, and determining a predicted dose distribution of the target object according to the image of the target object; and determining an objective dose distribution for the radiation delivery plan based on the predicted dose distribution and a plan-quality control strategy.

17 Claims, 10 Drawing Sheets

METHOD AND DEVICE FOR DETERMINING RADIATION DELIVERY PLAN, AND COMPUTER EQUIPMENT

CROSS-REFERENCE TO RELATED APPLICATION

The present application claims the priority of Chinese patent application No. 202311044767.X, filed on Aug. 17, 2023, and entitled "METHOD AND DEVICE FOR DETERMINING RADIATION DELIVERY PLAN, COMPUTER EQUIPMENT, STORAGE MEDIUM AND COMPUTER PROGRAM PRODUCT", which is incorporated herein by reference in its entirety.

TECHNICAL FIELD

The present application relates to the field of radiation, and in particular to a method and a device for determining a radiation delivery plan, a computer equipment, storage medium and a computer program product.

BACKGROUND

For radiation delivery (e.g., radiotherapy, radiation processing, or radiation flaw detection), it is usually necessary to make a delivery plan before delivery to ensure that an appropriate amount of radiation is delivered to a region of interest of a target object without harming the user or other parts of the target object. How to develop a suitable and optimal delivery plan has always been a hot problem in the industry.

As an example, the intensity-modulated radiotherapy plan among the radiation delivery plans is currently the most widely used treatment mode. The goal of the intensity-modulated radiotherapy plan is to ensure that the target region receives a sufficient dose of radiation to minimize the dose to the endangered organs and surrounding normal tissues.

In the related art, for the intensity-modulated radiotherapy plan, parameters such as a target dose and a weight factor thereof, and a tolerance dose of the organ-at-risk region and a weight factor thereof need to be set manually. The user needs to adjust and optimize the parameters in the process of making the intensity-modulated radiotherapy plan, thus consuming a lot of time and energy.

SUMMARY

In view of this, it is necessary to provide a method and a device for determining a radiation delivery plan, a computer equipment, a storage medium and a computer program product without setting parameters manually.

In a first aspect, the present application provides a method for determining a radiation delivery plan. The method includes: obtaining an image of a target object, and determining a predicted dose distribution of the target object according to the image of the target object; and determining an objective dose distribution for the radiation delivery plan based on the predicted dose distribution and a plan-quality control strategy.

In one of the embodiments, the plan-quality control strategy comprises at least one of a priority control strategy, an off-target dose control strategy, a conformance control strategy, a hot spot control strategy, a target region dose control strategy, a uniformity control strategy, or an automatic normalization control strategy.

In one of the embodiments, the plan-quality control strategy comprises different control strategies.

In one of the embodiments, determining the objective dose distribution for the radiation delivery plan based on the predicted dose distribution and the plan-quality control strategy includes: determining the objective dose distribution for the radiation delivery plan by stages, based on one of or a combination from the different control strategies and the predicted dose distribution per stage.

In one of the embodiments, the plan-quality control strategy includes at least one of: the priority control strategy, the off-target dose control strategy, the conformance control strategy, the hot spot control strategy, the target region dose control strategy, the uniformity control strategy, or the automatic normalization control strategy.

In one of the embodiments, the different control strategies comprise the priority control strategy, the off-target dose control strategy, the conformance control strategy, the hot spot control strategy, the target region dose control strategy, the uniformity control strategy, and the automatic normalization control strategy. Determining the objective dose distribution for the radiation delivery plan by stages, based on one of or the combination from the different control strategies and the predicted dose distribution includes: obtaining a first dose-calculating function based on the conformance control strategy and the off-target dose control strategy and the predicted dose distribution, and optimizing the first dose-calculating function to obtain a first dose distribution; obtaining a second dose-calculating function based on the first dose distribution and the target region dose control strategy, and optimizing the second dose-calculating function to obtain a second dose distribution; obtaining a third dose-calculating function based on the second dose distribution and the priority control strategy and the hot spot control strategy, and optimizing the third dose-calculating function to obtain a third dose distribution; and obtaining an objective dose-calculating function based on the third dose distribution and the uniformity control strategy, and optimizing the objective dose-calculating function to obtain an optimized dose distribution, and processing the optimized dose distribution by using the automatic normalization control strategy to obtain the objective dose distribution.

In one of the embodiments, the conformance control strategy is: $f_1=\omega_1\times(f_{C1}-C_{index})^2$, wherein $\omega_1$ is a preset parameter, $C_{index}=1$ represents that a desired conformity to be controlled between a region covered by a prescription dose and the target region is 1, $f_{C1}$=TV_RI×TV_RI/(V_RI×TV), wherein TV_RI represents a volume of an intersection region between the region covered by the prescription dose and the target region, V_RI represents a volume of the region covered by the prescription dose, and TV represents a volume of the target region.

The off-target dose control strategy $f_2$ is: $f_2=\omega_2\times\Sigma(\max(D_i-D_{i,pre}, 0))^2$, where $\omega_2$ is a preset parameter, $D_i$ represents a dose corresponding to an i-th voxel to be optimized in the image, and $D_{i,pre}$ represents a dose corresponding to an i-th voxel in the predicted dose distribution.

The first dose-calculating function is $F=f_1+f_2$.

In ones of the embodiments, the target region dose control strategy $f_3$ is: $f_3=\omega_3\times\Sigma(\min(D_i-D_{prescription},0))^2$, wherein $\omega_3$ is a pre-set parameter, and $D_{prescription}$ represents a prescription dose; and the second dose-calculating function is: $F_2=f_3$.

In one of the embodiments, determining the objective dose distribution for the radiation delivery plan based on the predicted dose distribution and the plan-quality control strategy, includes: constructing an initial dose-calculating function based on the predicted dose distribution; obtaining an objective dose-calculating function based on the initial dose-calculating function and the plan-quality control strategy; and computing the objective dose-calculating function to obtain the objective dose distribution.

In one of the embodiments, determining the objective dose distribution for the radiation delivery plan based on the predicted dose distribution and the plan-quality control strategy, includes: selecting any control strategy from the plan-quality control strategy as a current control strategy; optimizing a current dose distribution according to the current control strategy to obtain an optimized dose distribution; and using the optimized dose distribution as an updated current dose distribution, and using any remaining control strategy in the plan-quality control strategy as an updated current control strategy, returning to execute step of optimizing the current dose distribution according to the current control strategy to obtain the optimized dose distribution, until all control strategies of the plan-quality control strategy are traversed, and using the optimized dose distribution obtained finally as the objective dose distribution.

In one of the embodiments, obtaining the image of the target object and determining the predicted dose distribution of the target object according to the image of the target object includes: obtaining the image of the target object, inputting the image of the target object into a dose-distribution predicting model to obtain the predicted dose distribution.

In one of the embodiments, obtaining the image of the target object, and inputting the image of the target object into a dose-distribution predicting model to obtain the predicted dose distribution, include: obtaining the image of the target object, and inputting the image of the target object into the dose-distribution predicting model to obtain an initial dose distribution; and adjusting the initial dose distribution according to dose distribution reference information to obtain the predicted dose distribution, where the dose distribution reference information includes at least one of an objective dose of a target region in the image, a dose limit of an organ-at-risk region in the image, or a priority of the organ-at-risk region.

In one of the embodiments, the objective dose of the target region in the image refers to a prescription dose set for the target region in the image according to specificity of the image. The dose limit of the organ-at-risk region in the image refers to a lower limit of unacceptable dose set for the organ-at-risk region outside the target in the image. The priority of the organ-at-risk region refers to the priority of the organ-at-risk region relative to the target region.

In one of the embodiments, the priority of the organ-at-risk region includes a high priority, a medium priority, and a low priority. The high priority defines that the priority of the organ-at-risk region is higher than the priority of the target region, and that the minimum value between the dose limit of the organ-at-risk region and the initial dose distribution is selected to be the dose distribution of the organ-at-risk region in the predicted dose distribution. The medium priority defines that the dose distribution of the organ-at-risk region in the predicted dose distribution is determined according to the initial dose distribution. The low priority defines that the priority of the target region is higher than that of the organ-at-risk region, and that the target region is necessarily ensured to have a sufficient irradiation dose, and that the dose distribution of the organ-at-risk region in the predicted dose distribution is determined according to the initial dose distribution.

In one of the embodiments, the priority of the organ-at-risk region includes a high priority, a medium priority, and a low priority.

Adjusting the initial dose distribution according to dose distribution reference information to obtain the predicted dose distribution, comprising: selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

In one of the embodiments, before inputting the image of the target object into the dose-distribution predicting model to obtain the predicted dose distribution, the method further includes: obtaining a training sample image set, contouring a target region (and optionally an organ-at-risk region) in the training sample image set, and obtaining gold standard dose information of a dose distribution in the target region and outside the target region; inputting the contoured training sample image set and the gold standard dose information into an initial neural network, and performing an iterative training according to a preset loss function, until a preset iteration condition is met to obtain the dose-distribution predicting model.

In one of the embodiments, the preset iteration condition is a preset number of iterations, or a convergence accuracy of the preset loss function.

In one of the embodiments, the image of the target object is a computed tomography image, a magnetic resonance image, an X-ray image, or an ultrasound image of the target object.

In one of the embodiments, the predicted dose distribution is a fluence diagram, a numerical value, or a mathematical model.

In one of the embodiments, the radiation delivery plan is configured to characterize machine parameters corresponding to a situation that the target region has sufficient irradiation dose while an irradiation dose outside the target region is minimized.

The present application further provides a method for determining a radiation delivery plan, and the method includes: obtaining an image of a target object; determining an initial dose distribution based on the image of the target object; determining a predicted dose distribution of the target object by adjusting the initial dose distribution according to dose distribution reference information; and determining an objective radiation delivery plan based on the predicted dose distribution.

In one of the embodiments, the dose distribution reference information including at least one of an objective dose of the target region in the image, a dose limit of the organ-at-risk region in the image, or a priority of the organ-at-risk region.

In one of the embodiments, determining the initial dose distribution based on the image of the target object includes: inputting the image of the target object into a dose-distribution predicting model to obtain the initial dose distribution.

In one of the embodiments, the target object includes a target region and an organ-at-risk region. The object table comprises at least one of an objective dose of the target region in the image, a dose limit of the organ-at-risk region in the image, or a priority of the organ-at-risk region.

The priority of the organ-at-risk region includes a high priority, a medium priority, and a low priority.

Determining the predicted dose distribution of the target object by adjusting the initial dose distribution according to the dose distribution reference information includes: selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

In one of the embodiments, determining the objective radiation delivery plan based on the predicted dose distribution, comprising: determining an objective dose distribution for the radiation delivery plan based on the predicted dose distribution and a plan-quality control strategy; and determining the objective radiation delivery plan based on the objective dose distribution.

In one of the embodiments, the plan-quality control strategy comprises different control strategies of a priority control strategy, an off-target dose control strategy, a conformance control strategy, a hot spot control strategy, a target region dose control strategy, a uniformity control strategy, and an automatic normalization control strategy; and determining the objective dose distribution for the radiation delivery plan based on the predicted dose distribution and the plan-quality control strategy comprises: determining the objective dose distribution for the radiation delivery plan by stages, based on one of or a combination from the different control strategies and the predicted dose distribution per stage.

In a second aspect, the present application further provides a device for determining a radiation delivery plan, and the device includes: circuitry of a predicted dose distribution determination module and circuitry of an objective dose distribution determination module.

The circuitry of the predicted dose distribution determination module is configured to obtain an image of a target object, and determine a predicted dose distribution of the target object according to the image of the target object.

The circuitry of an objective dose distribution determination module is configured to determine an objective dose distribution for the radiation delivery plan based on the predicted dose distribution and a plan-quality control strategy.

In a third aspect, the present application further provides a computer equipment, including a memory and a processor. The memory has a computer program stored thereon, and the processor, when executing the computer program, performs steps of any method provided in the first aspect.

In a fourth aspect, the present application further provides a non-transitory computer-readable storage medium, having computer-executable instructions stored thereon. The computer-executable instructions, when executed by a processor, perform steps of any method provided in the first aspect.

In a fifth aspect, the present application further provides a computer program product, including a computer program. The computer program, when executed by a processor, performs steps of any method provided in the first aspect.

As for the above-mentioned method and device for determining the radiation delivery plan, the computer equipment, the storage medium and the computer program product, the method includes obtaining an image of a target object, and determining a predicted dose distribution of the target object according to the image of the target object, and determining an objective dose distribution for the radiation delivery plan based on the predicted dose distribution and a plan-quality control strategy. In this embodiment, the dose distribution is optimized by using the plan-quality control strategy and the predicted dose distribution to obtain the objective dose distribution, so that the objective dose distribution for the radiation delivery plan may be obtained according to the objective dose distribution. In this way, the objective dose distribution for the radiation delivery plan may be determined directly according to the plan-quality control strategy and the predicted dose distribution, without consuming a lot of time and energy of the user, and a more accurate and more precise objective dose distribution may be determined, thereby obtaining a more accurate radiation delivery plan, and ensuring that a radiation delivery is implemented according to the objective radiation delivery plan to perform a radiotherapy on the target object.

DETAILED DESCRIPTION OF THE EMBODIMENTS

In order to make the purposes, technical solutions and advantages of the present application clearer and to be better understood, the present application is further described in detail hereinafter in conjunction with the accompanying drawings and embodiments. It should be understood that the specific embodiments described herein are only used to explain the present application but not used to limit the present application.

The serial numbers assigned to the components in this disclosure, such as “first”, “second”, etc., are only used to distinguish the described objects from each other, but not used to define an order or a technical meaning.

Before specifically describing the technical solutions of the embodiments of the present application, the technical background and technical evolution context on which the embodiments of the present application are based are introduced first. An intensity-modulated radiotherapy plan is the most widely used treatment mode at present, and the goal of the intensity-modulated radiotherapy plan is to adjust the irradiation dose of the region of interest, that is, to make the target region to be irradiated with a sufficient dose, and minimize the irradiation dose to the endangered organs and the surrounding normal tissue regions. In the related art, the intensity-modulated radiotherapy plan needs to rely on manual setting of parameters, such as the target region dose and the weight factor thereof, the tolerance dose of the endangered organ and the weight factor thereof. The user needs to repeatedly adjust and optimize the parameters in the process of making the intensity-modulated radiotherapy plan, thus consuming a lot of time and energy. In addition, the experience of the user and the time invested in making the intensity-modulated radiotherapy plan have a direct impact on the intensity-modulated radiotherapy plan. In view of this, the present application provides a method for determining a radiation delivery plan, which can be used to automatically make and optimize the plan.

Figure 1A:
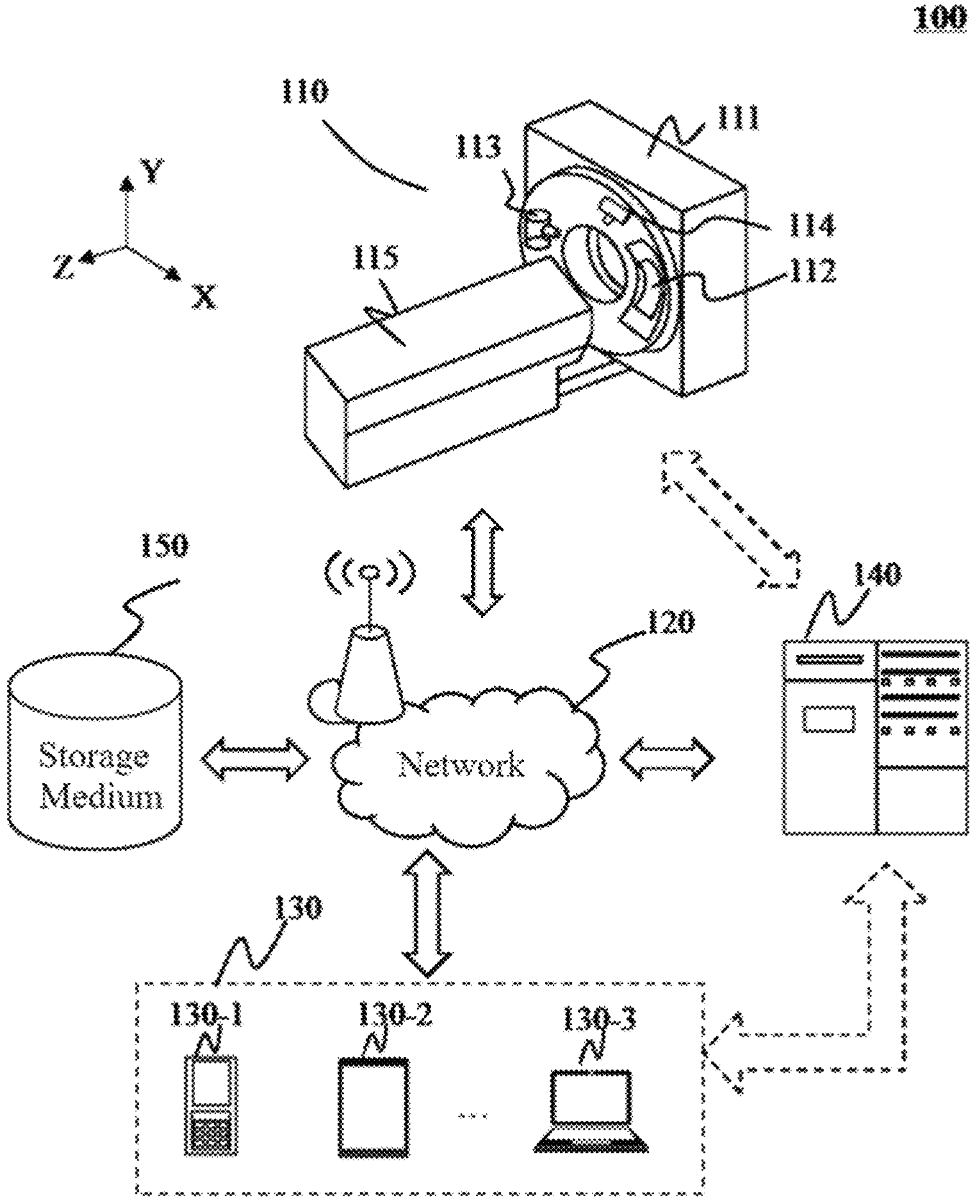
FIG. 1*a* is a view showing an application scenario of the present disclosure.

The technical solutions involved in the embodiments of the present application are described in combination with a scenario in which embodiments of the present application are applied. FIG. 1*a* is a view showing an application scenario according to some embodiments of the present application. As shown in FIG. 1*a*, the radiation system 100 may include a therapeutic radiation delivery device 110 and a computer equipment. The computer equipment may include a network 120, at least one terminal 130, a processing device 140, and a storage medium 150. The components of the radiation system 100 may be connected in a variety of ways. Exemplarily, the therapeutic radiation delivery apparatus 110 may be connected to the processing device 140 via the network 120. As another example, the therapeutic radiation delivery device 110 may be directly connected to the processing device 140, as indicated by the double-headed arrows in the dashed lines connecting the therapeutic radiation delivery device 110 and the processing device 140. As yet another example, the storage medium 150 may be connected to the processing device 140 directly or through the network 120. As another example, the terminal 130 may be connected to the processing device 140 directly (as indicated by the double-headed arrows in the dashed lines connecting the terminal 130 and the processing device 140) or through the network 120.

The therapeutic radiation delivery device 110 may include an imaging assembly, a first radiation source 114 or a therapeutic radiation source, a gantry 111, and a table 115. The imaging component may include a conventional CT (e.g., a fan beam CT), a cone beam CT (CBCT), a spiral CT, multi-slice CT, PET-CT, etc., or any combination thereof. The imaging assembly may be used to generate at least one image before, during, or after a radiation therapy. As shown in FIG. 1*a*, the imaging assembly may include a second or imaging radiation source 113 (e.g., an X-ray tube) and a detector module 112. The gantry 111 may include a rotating ring (not shown in FIG. 1*a*), and the rotating ring may be used to accommodate the second radiation source 113, the detector module 112 and the first radiation source 114. The object may be placed on the table 115 and moved along the Z-axis direction. The object may be a biological object (e.g., a patient, an animal), or a non-biological object (e.g., a man-made object).

Figure 1B:
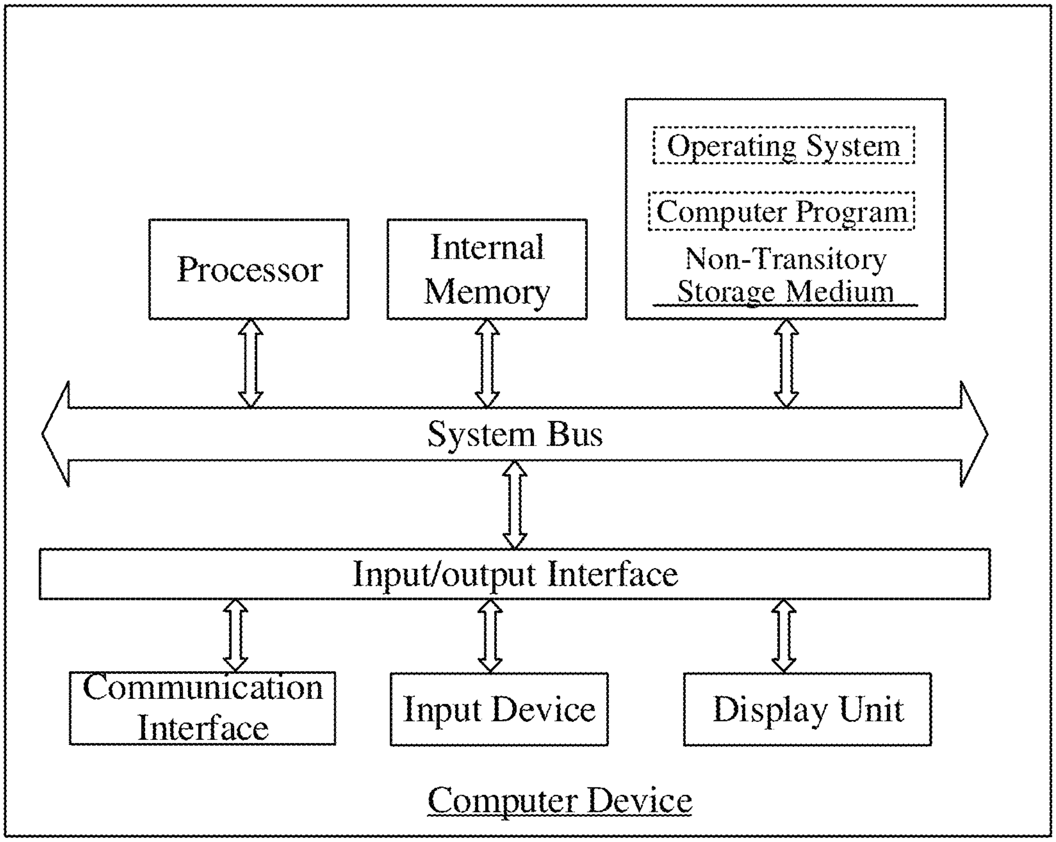
FIG. 1*b* is a view showing a structure of a computer equipment according to an embodiment of the present application.

The method for determining the radiation delivery plan provided in the present application may be applied to the computer equipment of the radiation system 100, and an internal structure of the computer equipment is shown in FIG. 1*b*. The computer equipment includes a processor, a memory, a communication interface, a display screen, and an input device, which are connected by a system bus. The processor of the computer equipment is configured to provide computing and control capabilities. The memory of the computer equipment includes a non-transitory storage medium and an internal memory. The non-transitory storage medium stores an operating system and a computer program. The internal memory provides an environment for the operation of the operating system and the computer program in the non-transitory storage medium. The communication interface of the computer equipment is configured to communicate with an external terminal in a wired or wireless manner, and the wireless manner may be implemented through WIFI, a mobile cellular network, a near field communication (NFC), or other technologies. The computer program, when executed by the processor, executes a method for determining a radiation delivery plan. The display screen of the computer equipment may be a liquid crystal display screen or an electronic ink display screen. The input device of the computer equipment may be a touch layer covered on the display screen, a key, a trackball or a touch pad arranged on the housing of the computer equipment, or may be an external keyboard, an external touch pad or an external mouse.

Figure 2:
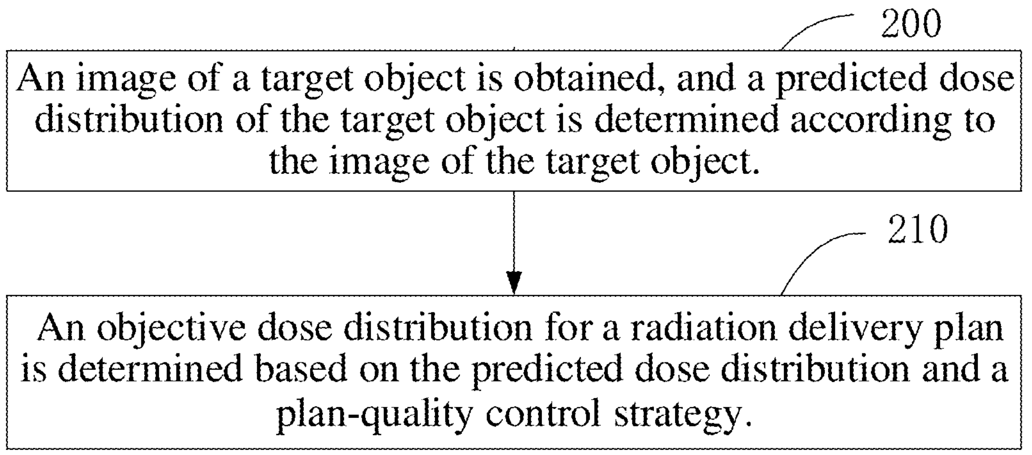
FIG. 2 is a schematic flow chart of steps of a method for determining a radiation delivery plan according to an embodiment of the present application.

In an embodiment, as shown in FIG. 2, the present application provides a method for determining a radiation delivery plan, and this embodiment is illustrated exemplarily by being applied to the computer equipment. In this embodiment, the method includes steps 200 and 210.

In Step 200, an image of a target object is obtained, and a predicted dose distribution of the target object is determined according to the image of the target object.

The target object may refer to any one of a human body or a part of a human body (e.g., a tissue, an organ, or any other combination thereof), a whole water film or a part of a water film, an object to be irradiated or a part of the object, an experimental body or a part of an experimental body, and a specific space (e.g., a region of interest or a volume of interest), which are not limited in this embodiment.

The image of the target object may be a computed tomography (CT) image, a magnetic resonance (MR) image, an X-ray image, or an ultrasound image of the target object. A device for determining the radiation delivery plan or a computer equipment may obtain the image of the target object from a post-processing workstation of an imaging equipment, or may obtain the image of the target object from a Picture Archiving and Communication Systems (PACS) server. The image of the target object is a three-dimensional image.

The predicted dose distribution refers to predicted doses of radiation towards regions of the target object and the predicted dose distribution position. The predicted dose distribution may be presented in various forms, such as a fluence map, a dose and volume histogram (DVH) curve, a three-dimensional (3D) dose distribution reconstruction etc.

The predicted dose distribution of the target object may be determined in various ways, for example, by obtaining the predicted dose distribution of the target object from a storage medium of the computer equipment or by calculating the predicted dose distribution using the computing device.

In Step 210, an objective dose distribution for a radiation delivery plan is determined based on the predicted dose distribution and a plan-quality control strategy.

The plan-quality control strategy may be a strategy preset by the user to optimize the dose distribution. The plan-quality control strategy may be pre-stored in the computer equipment by the user.

After obtaining the predicted dose distribution, the computer equipment may adjust the machine parameters by using the plan-quality control strategy, thereby optimizing the dose distribution and obtaining the objective dose distribution for the radiation delivery plan. The radiation delivery plan is used to characterize the machine parameters corresponding to the situation that the target region has sufficient irradiation dose while the irradiation dose outside the target region is minimized. The machine parameters may include a leaf position, monitor units (MUs) of the machine, etc. The leaf position may refer to the position of the leaves of the multi-leaf collimator during the radiotherapy, which corresponds to the segment shape at respective control points. In addition, other methods may also be used to optimize the dose distribution by using the plan-quality control strategy. As a non-limiting example, the plan-quality control strategy may be used to optimize the fluence map corresponding to the predicted dose distribution, and the optimized fluence map may be used to determine various parameters (for example, an intensity, a width and a duration of a pulse, etc.) related to the radiation delivery. For another example, the plan-quality control strategy may be used to optimize the distribution map corresponding to the predicted dose distribution, and the optimized dose distribution map may be used to determine the machine parameters of the radiation delivery machine which performs a radiation delivery.

In this embodiment, the dose distribution is optimized by using the plan-quality control strategy and the predicted dose distribution to obtain the objective dose distribution, so that the objective dose distribution for the radiation delivery plan may be obtained according to the objective dose distribution. In this way, the objective radiation delivery plan may be determined directly according to the plan-quality control strategy and the predicted dose distribution, without consuming a lot of time and energy of the user, and a more accurate and more precise objective dose distribution may be determined, thereby obtaining a more accurate radiation delivery plan, and ensuring that a radiation delivery is implemented according to the objective radiation delivery plan to perform a radiotherapy on the target object.

In an embodiment, the plan-quality control strategy may include at least one of a priority control strategy, an off-target dose control strategy, a conformance control strategy, a hot spot control strategy, a target region dose control strategy, a uniformity control strategy, or an automatic normalization control strategy, as well as other strategies for controlling plan quality. As an example, the plan-quality control strategy may include one of the above-mentioned strategies. As another example, the plan-quality control strategy may include multiple strategies. During a plan optimization, the plan quality may be controlled by using a combination of plan control strategies, so that the result obtained by optimizing once may meet the plan requirements set by the user. The design of the plan-quality control strategy may be an abstraction of at least one of the focus points in a manual plan design and in an evaluation process. The combination of plan control strategies may be a strategy combination determined by taking a consideration of at least one of a certain sequence and a weight during an optimization, thereby obtaining an automatically optimized high precise plan that meets clinical requirements.

The plan-quality control strategy may include one or more of the priority control strategies, the off-target dose control strategy, the conformance control strategy, the hot spot control strategy, the target region dose control strategy, the uniformity control strategy and the automatic normalization control strategy. The priority control strategy is used to characterize the optimization of the dose distribution, which is performed according to a set priority. The off-target dose control strategy is used to characterize the optimization of the irradiation dose outside the target region in the predicted dose distribution. The conformance control strategy is used to characterize the optimization of a matching degree between the prescription dose line region and the target region in the predicted dose distribution. The hot spot control strategy is used to characterize the control of a hot spot in the target region in the predicted dose-distribution. The target region dose control strategy is used to characterize the optimization of the irradiation dose of the target region in the predicted dose distribution. The uniformity control strategy is used to characterize the optimization of the uniformization of the irradiation dose of the target region in the predicted dose distribution. The automatic normalization control strategy is used to characterize the normalization of the irradiation dose of the target region in the predicted dose distribution.

In this embodiment, multiple plan-quality control strategies are provided, and the user may select one or more of the multiple plan-quality control strategies to optimize the dose distribution according to actual needs, such that the practicality of the method for determining the radiation delivery plan may be improved.

In the embodiments of the present application, an iterative optimization algorithm is used to optimize the dose distribution. Exemplary iterative optimization algorithms may include a simulated annealing (SA) algorithm, an algebraic inverse process planning (AITP) algorithm, a simultaneous iterative inverse process planning (SIITP) algorithm, a Monte Carlo (MC) algorithm, a pencil beam convolution (PBC) algorithm, a gradient-based algorithm (e.g., a conjugate gradient algorithm, or a quasi-Newton algorithm), a genetic algorithm, a neural network-based algorithm, etc., or any combination thereof. In some embodiments, at least one iterative optimization algorithm may be used in the iterations. For example, in the first part of the iteration (e.g., from the first iteration to the n-th iteration), the simulated annealing algorithm may be used, while in the second part of the iteration (e.g., from the (N+1)-th to the M-th iteration, M>N), the gradient-based algorithm may be used.

Figure 3:
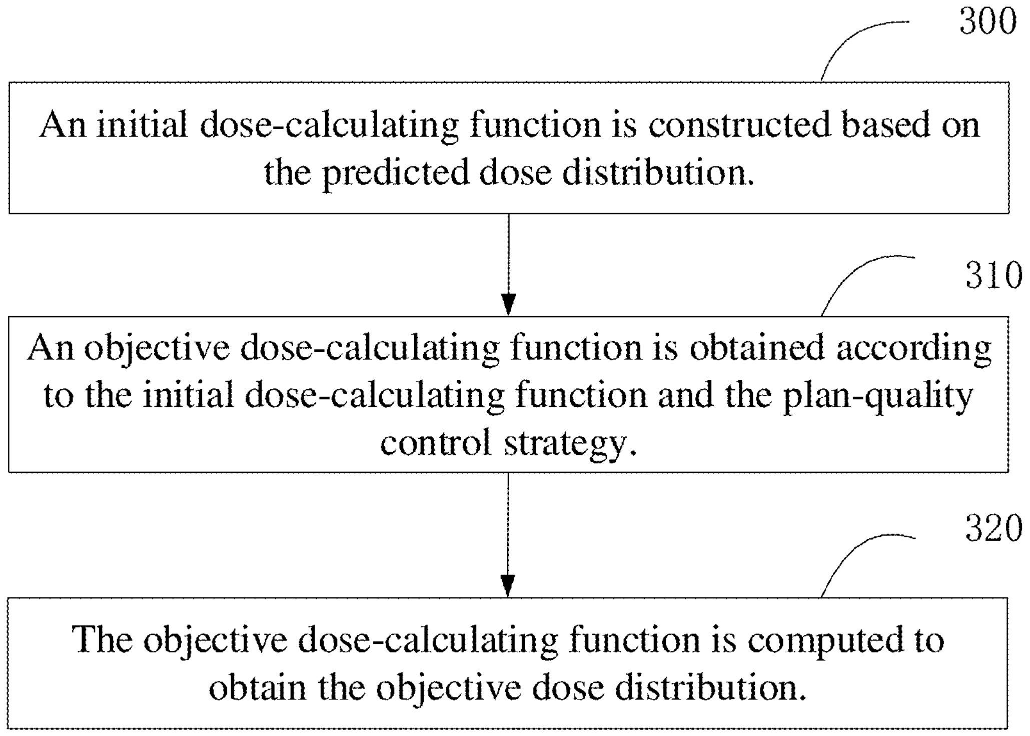
FIG. 3 is a schematic flow chart of steps of the method for determining the radiation delivery plan according to another embodiment of the present application.

In an embodiment, as shown in FIG. 3, an implementation of step 210 of determining the objective dose distribution for the radiation delivery plan based on the predicted dose distribution and the plan-quality control strategy is provided, and steps of the implementation may include step 300 to step 320.

In Step 300, an initial dose-calculating function is constructed based on the predicted dose distribution.

After obtaining the predicted dose distribution of the target object, the computer equipment constructs the initial dose-calculating function based on the predicted dose distribution. The initial dose-calculating function may be expressed by using a relationship between the predicted dose distribution and a dose distribution to be optimized. In an embodiment, the relationship between the predicted dose distribution and the dose distribution to be optimized may be an operation relationship.

In Step 310, an objective dose-calculating function is obtained according to the initial dose-calculating function and the plan-quality control strategy.

After the computer equipment obtains the initial dose-calculating function, the objective dose-calculating function is obtained according to the initial dose-calculating function and the plan-quality control strategy. In an embodiment, the objective dose-calculating function may be obtained by adding the initial dose-calculating function and the plan-quality control strategy. For the description of the plan-quality control strategy, please refer to the specific description in the above embodiments.

In Step 320, the objective dose-calculating function is computed (namely optimized) to obtain the objective dose distribution.

The computer equipment obtains the objective dose-calculating function, and the objective dose-calculating function characterizes the relationship between the predicted dose distribution and the objective dose distribution to be optimized. After the objective dose-calculating function is computed (namely optimized), the optimized dose distribution, namely the objective dose distribution, is obtained. The radiation delivery plan may be determined based on the objective dose distribution.

In an embodiment, computing the objective dose-calculating function refers to making the value of the objective dose-calculating function approach zero as proximately as possible through an iterative calculation.

In an embodiment, a corresponding relationship between a dose distribution and a radiation delivery plan is pre-stored in the computer equipment. After obtaining the objective dose distribution, the computer equipment searches for a radiation delivery plan corresponding to the dose distribution in the computer equipment that is the same as the objective dose distribution, and determines the radiation delivery plan to be the objective radiation delivery plan.

In this embodiment, the initial dose-calculating function constructed according to the predicted dose distribution is optimized by using the plan-quality control strategy to obtain the objective dose-calculating function, and the objective dose distribution is obtained by computing the objective dose-calculating function. In this way, the objective dose distribution can be determined quickly, thus determining the objective radiation delivery plan quickly, thereby improving the practicality and efficiency of the method for determining the radiation delivery plan.

Figure 4:
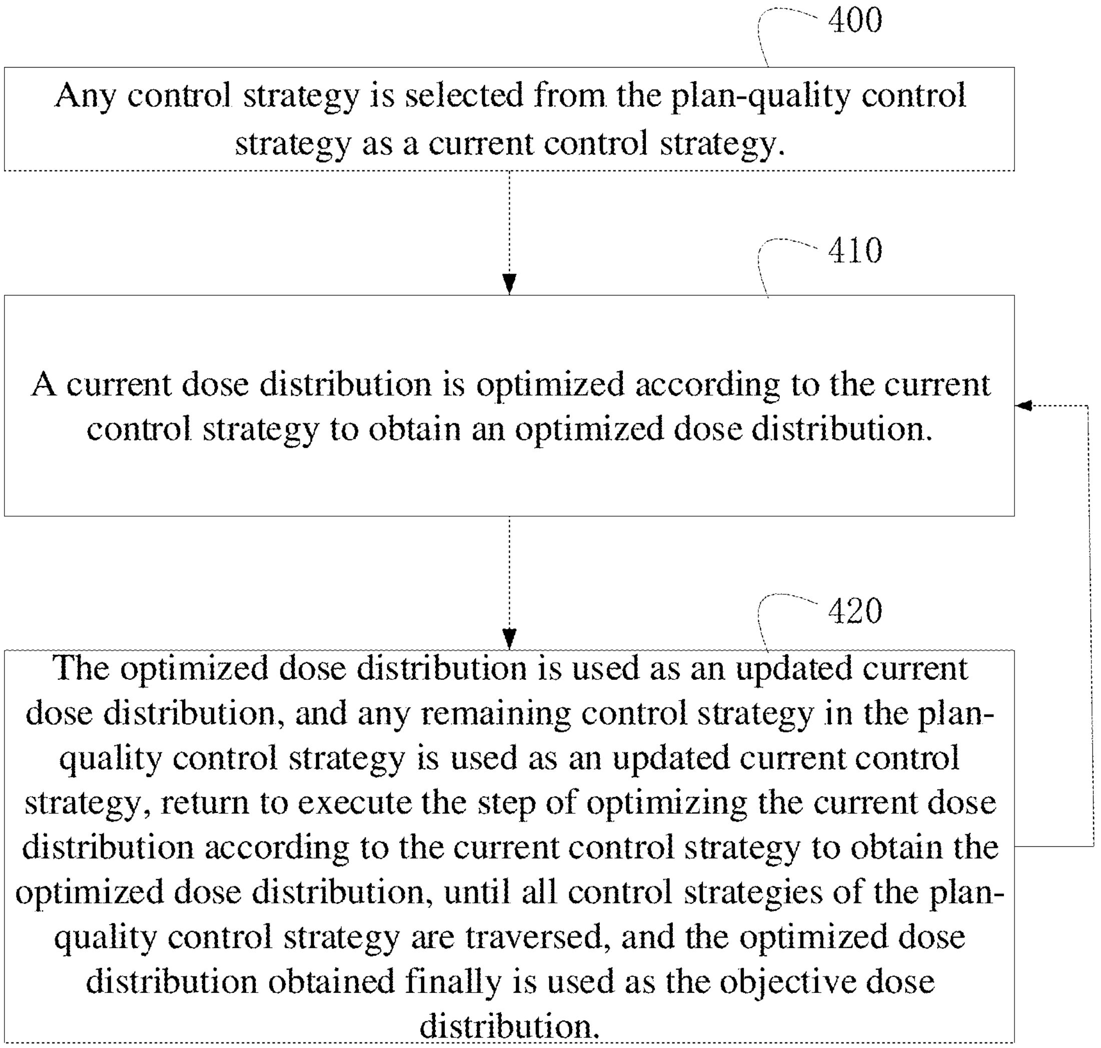
FIG. 4 is a schematic flow chart of steps of the method for determining the radiation delivery plan according to yet another embodiment of the present application.

In an embodiment, when the plan-quality control strategy includes multiple control strategies, as shown in FIG. 4, an implementation of step 210 of determining the objective dose distribution for the radiation delivery plan based on the predicted dose distribution and the plan-quality control strategy is provided, and steps of the implementation include step 400 to step 420.

In Step 400, any control strategy is selected from the plan-quality control strategy as a current control strategy.

When the plan-quality control strategy includes at least two of the priority control strategy, the off-target dose control strategy, the conformance control strategy, the hot spot control strategy, the target region dose control strategy, the uniformity control strategy, or the automatic normalization control strategy, the computer equipment selects any control strategy from the plan-quality control strategy including multiple control strategies as the current control strategy.

In Step 410, a current dose distribution is optimized according to the current control strategy to obtain an optimized dose distribution. In some embodiments of the present application, in an iterative calculation, the current dose distribution in this step may be a preset dose distribution.

After the computer equipment determines the current control strategy, the current dose distribution is optimized by using the current control strategy to obtain the optimized dose distribution. The process of optimizing the dose distribution by using the current control strategy is related to the type of the selected target control strategy, and optimization methods for the selected target control strategies of different types are different.

In Step 420, the optimized dose distribution is used as an updated current dose distribution, and any remaining control strategy in the plan-quality control strategy is used as an updated current control strategy, return to execute the step of optimizing the current dose distribution according to the current control strategy to obtain the optimized dose distribution, until all control strategies of the plan-quality control strategy are traversed, and the optimized dose distribution obtained finally is used as the objective dose distribution.

After obtaining the optimized dose distribution, the computer equipment uses the optimized dose distribution as the updated current dose distribution, reselects any control strategy from the remaining control strategies in the plan-quality control strategy as the updated current control strategy, and returns to execute step 410, until all control strategies of the plan-quality control strategy are traversed, and the optimized dose distribution obtained in the last cycle is used as the objective dose distribution.

In this embodiment, when the plan-quality control strategy includes a plurality of control strategies, the dose distribution is optimized using the plurality of control strategies, thereby obtaining an optimal objective dose distribution, and further obtaining a radiation delivery plan with higher quality.

In an embodiment, an implement of step 200 of obtaining the image of the target object, and determining the predicted dose distribution of the target object based on the image of the target object includes: obtaining the image of the target object, inputting the image of the target object into a dose-distribution predicting model to obtain the predicted dose distribution.

The target region, organ-at-risk regions and other tissue regions in the image of the target object are divided. In some embodiments, the computer equipment may input the acquired original image of the target object into a pre-trained classification model to obtain the divided image of the target object.

The dose-distribution predicting model may be pre-trained by a user and stored in the computer equipment, or it can be obtained by an on-site calculation or adjustment. After the computer equipment acquires the image including the target object, the image is inputted into the pre-trained dose-distribution predicting model, and outputs the predicted dose distribution from the dose-distribution predicting model.

In an embodiment, a method for training a dose-distribution predicting model includes: obtaining a training sample image set, contouring a target region (and optionally an organ-at-risk region) in the training sample image set, and obtaining gold standard dose information of the dose distribution in the target region and outside the target region; inputting the contoured training sample image set and the gold standard dose information into an initial neural network, and performing an iterative training according to a preset loss function, until a preset iteration condition is met to obtain the dose-distribution predicting model. The iteration condition may be the preset number of iterations, or a convergence accuracy of the preset loss function, etc. The initial neural network may be a 3D-UNet, a UNet, a 3D-UNet, or a VNet.

Figure 5:
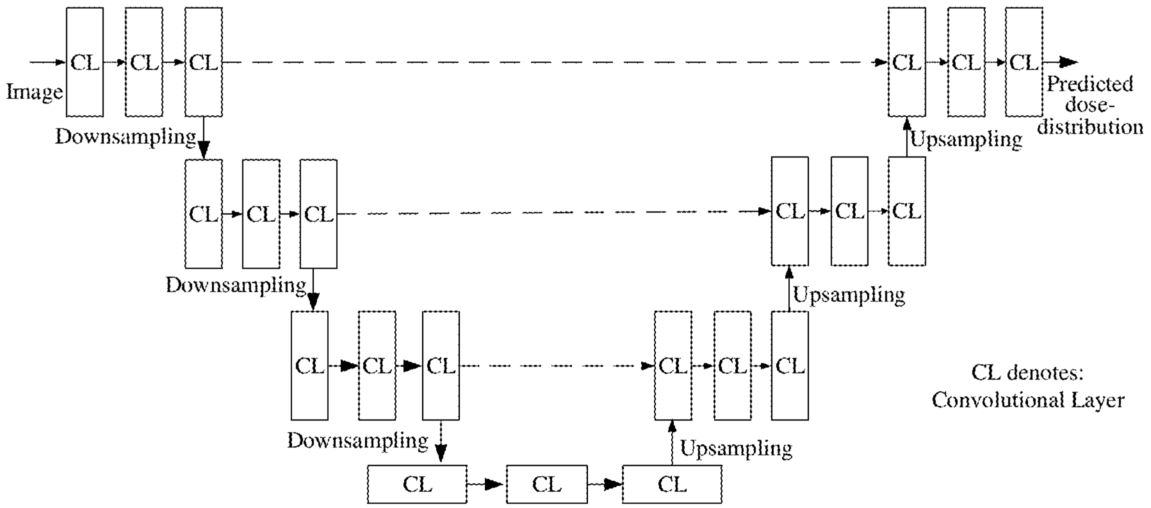
FIG. 5 is a view showing a structure of a dose-distribution predicting model according to an embodiment of the present application.

In an embodiment, the structure of the dose-distribution predicting model is shown in FIG. 5.

In this embodiment, the predicted dose distribution can be obtained by directly inputting the image including the target object into the pre-trained dose-distribution predicting model. Such a method of obtaining the predicted dose distribution is simple and fast.

Not limited thereto, in addition or alternatively, the dose-distribution predicting model may also be trained using other types of data, such as fluence maps, radiation experiment data, machine parameters, environmental conditions, patient physical conditions, etc., which are not limited herein. Accordingly, in addition to the imaging information or alternatively, other types of information, such as but not limited to a two-dimensional or three-dimensional model of the target region, and patient symptom data, may be inputted into the dose-distribution predicting model to obtain the predicted dose distribution.

Figure 6:
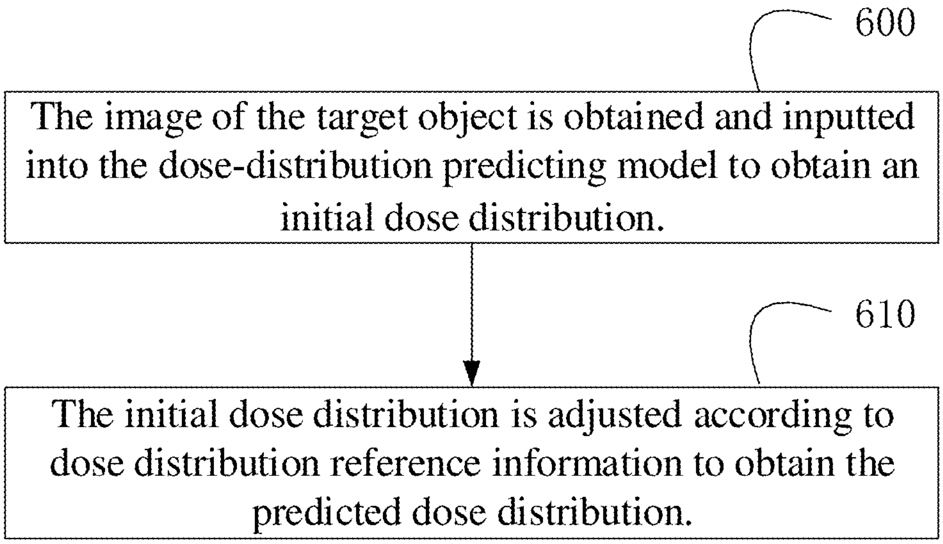
FIG. 6 is a schematic flow chart of steps of the method for determining the radiation delivery plan according to yet another embodiment of the present application.

In an embodiment, as shown in FIG. 6, an implementation of obtaining the image of the target object and inputting the image of the target object into the dose-distribution predicting model and obtaining the predicted dose distribution, is provided, and steps of the implementation include step 600 and step 610.

In Step 600, the image of the target object is obtained and inputted into the dose-distribution predicting model to obtain an initial dose distribution.

For the description of the dose-distribution predicting model, refer to the specific description in the above embodiment. The computer equipment inputs the obtained image into the pre-trained dose-distribution predicting model to obtain the initial dose distribution in the image.

In Step 610, the initial dose distribution is adjusted according to dose distribution reference information to obtain the predicted dose distribution. The dose distribution reference information includes at least one of an objective dose of a target region in the image, a dose limit of an organ-at-risk region in the image, or a priority of the organ-at-risk region.

Since an initial radiation delivery plan corresponding to the initial dose distribution cannot meet specific clinical requirements based on patient's conditions, the user may need to adopt a way to characterize the specific requirements for the plan quality. The dose distribution reference information, such as an objective table, provides abundant ways for the user to characterize the specific requirements for the plan, and the user can characterize the specific requirements for a plan in a personalized manner through the dose distribution reference information. As a non-limiting example, the dose distribution reference information may be set to include information such as a target region prescription dose, a limit requirement of an organ, and a set priority, where the information of the priority may characterize the importance of the target region relative to the organ and the importance of an organ relative to another organ.

The dose distribution reference information may be information preset by a user according to the specificity of the target object. The dose distribution reference information includes one or more of the objective dose of the target region in the image, the dose limit of the organ-at-risk region in the image, and the priority of the organ-at-risk region. The objective dose of the target region in the image refers to the prescription dose set for the target region in the image by the user according to the specificity of the image. The dose limit of the organ-at-risk region in the image refers to a lower limit of an unacceptable dose set by the user for the organ-at-risk region outside the target in the image. The priority of the organ-at-risk region refers to the priority of the organ-at-risk region relative to the target region. The priority of the organ-at-risk region may include a high priority, a medium priority, and a low priority. The high priority means that the priority of the organ-at-risk region is higher than the priority of the target region, that is, the dose limit for the organ-at-risk region in the image must be met, that is, the minimum value between the dose limit of the organ-at-risk region and the initial dose distribution is selected to be the dose distribution of the organ-at-risk region in the predicted dose distribution. The medium priority means that the organ-at-risk region is in a competitive relationship with the target region, and the irradiation dose of the organ-at-risk region is reduced while ensuring that the target region has a sufficient irradiation dose, that is, the dose distribution of the organ-at-risk region in the predicted dose distribution is determined according to the initial dose distribution. The low priority means that the priority of the target region is higher than that of the organ-at-risk region, and it is necessary to ensure that the target region has a sufficient irradiation dose, and the dose distribution of the organ-at-risk region in the predicted dose distribution is still determined according to the initial dose distribution. In one of the embodiments, adjusting the initial dose distribution according to dose distribution reference information to obtain the predicted dose distribution, including: selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

In an optional non-limiting embodiment, the dose distribution reference information may be as shown in the following table:

| Region in image including target object | Clinical target name | Limit for clinical target | Unit | Priority |
|---|---|---|---|---|
| XX | XX | XX | XX | High |
| XX | XX | XX | XX | Medium |
| XX | XX | XX | XX | Low |

In another optional non-limiting embodiment, the dose distribution reference information may be shown in the following table:

| Group | Name | Type | Set value | Unit | Priority | Description |
|---|---|---|---|---|---|---|
| | | | Target region | | | |
| | PTV | Prescription | 5000 | [cGy] | Medium | Prescription dose of a planned target volume (PTV) is set to 5000 cGy, and has a medium priority. |
| | PTV | Dmax | ≤5300 | [cGy] | Medium | The maximum dose of a planned target volume (PTV) is less than or equal to 5300 cGy, and has a |

-continued

| Group | Name | Type | Set value | Unit | Priority | Description |
|---|---|---|---|---|---|---|
| | | | | | | medium priority. |
| | CTV | Dmin | ≥5000 | [cGy] | High | The minimum dose of a clinical target volume (CTV) is greater than or equal to 5000 cGy, and has a high priority. |
| Organ-at-risk region | | | | | | |
| | Spinal cord | Dmax | ≤4500 | [cGy] | high | The maximum dose to the spinal cord is less than or equal to 4500 cGy, and has a high priority. |
| | Baldder | Dmean | ≤3000 | [cGy] | Medium | The average dose to the bladder is less than or equal to 3000 cGy, and has a medium priority. |
| | Baldder | D50 | ≤3000 | [cGy] | Medium | The dose to 50% volume of the bladder is less than or equal to 3000 cGy, and has a medium priority. |
| | Femoral head | V30 | ≤20 | [%] | Low | The volume corresponding to 3000 cGy to the femoral head is less than or equal to 20%, and has a low priority. |
| Auxiliary structure | | | | | | |
| | Ring | Dmax | ≤4950 | [cGy] | Low | The maximum dose of the ring is less than or equal to 4950 cGy, and has a low priority. |

After obtaining the initial dose distribution, the computer equipment uses at least one type of the dose distribution reference information to adjust the initial dose distribution to obtain the predicted dose distribution.

In this embodiment, the initial dose distribution obtained according to the dose-distribution predicting model is adjusted based on the dose distribution reference information, thereby obtaining an optimized predicted dose distribution, and further obtaining an optimized objective dose distribution for the radiation delivery plan.

In an embodiment, Step 210 of determining the objective dose distribution for the radiation delivery plan based on the predicted dose distribution and the plan-quality control strategy comprises: determining the objective dose distribution for the radiation delivery plan sequentially based on one or more different control strategies and the predicted dose distribution.

Figure 7:
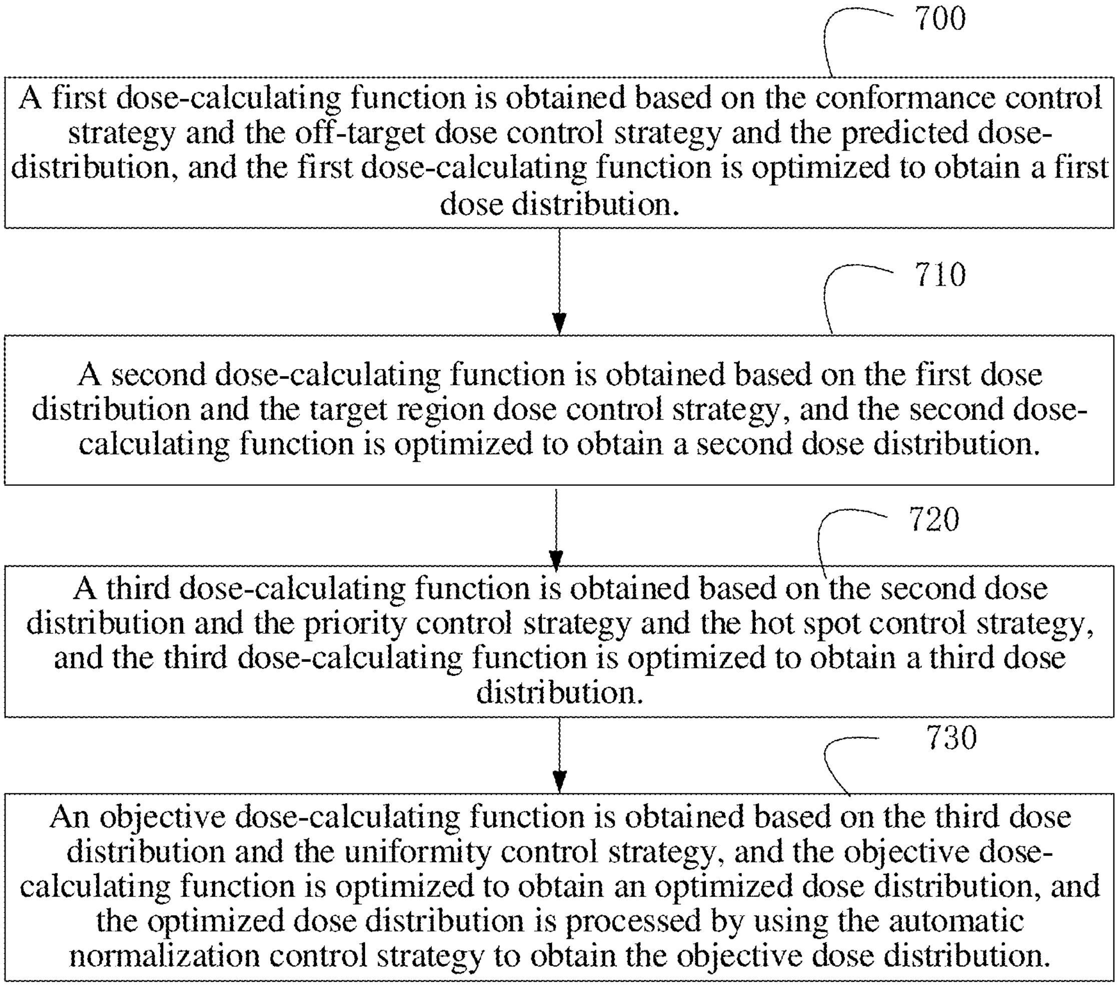
FIG. 7 is a schematic flow chart of steps of the method for determining the radiation delivery plan according to yet another embodiment of the present application.

In an embodiment, when the plan-quality control strategy includes different control strategies of: the priority control strategy, the off-target dose control strategy, the conformance control strategy, the hot spot control strategy, the target region dose control strategy, the uniformity control strategy, and the automatic normalization control strategy. Determining the objective dose distribution for the radiation delivery plan based on the predicted dose distribution and the plan-quality control strategy comprises: determining the objective dose distribution for the radiation delivery plan by stages, based on one of or a combination from the different control strategies and the predicted dose distribution per stage. That is, for example, as a first stage, a first dose distribution is obtained based on one of or a combination from the different control strategies and the predicted dose distribution. At a second stage, a second dose distribution is obtained based on one of or a combination from the different control strategies and an updated predicted dose distribution. At a third stage, a third dose distribution is obtained based on one of or a combination from the different control strategies and an updated predicted dose distribution, and so on. The dose distribution obtained finally is used as the objective dose distribution for the radiation delivery plan. As shown in FIG. 7, an implementation of determining the objective dose distribution for the radiation delivery plan by stages, based on one of or a combination from the different control strategies and the predicted dose distribution per stage is provided, and steps of the implementation include step 700 to step 730.

In Step 700, a first dose-calculating function is obtained based on the conformance control strategy and the off-target dose control strategy and the predicted dose distribution, and the first dose-calculating function is optimized to obtain a first dose distribution.

When the computer equipment optimizes the dose distribution, the dose distribution may be optimized based on the predicted dose distribution and by using the conformance control strategy and the off-target dose control strategy simultaneously. In some embodiments of the present application, the dose distribution may be optimized based on the predicted dose distribution and by using the conformance control strategy firstly, and then is optimized by using the off-target dose control strategy to obtain the first dose distribution. Alternatively, the dose distribution may be optimized based on the predicted dose distribution by using the off-target dose control strategy firstly, and then is optimized by using the conformance control strategy to obtain the first dose distribution.

In an embodiment, the conformance control strategy $f_1$ may be expressed as $f_1=\omega_1\times(f_{C1}-C_{index})^2$, where $\omega_1$ is a preset parameter, $C_{index}=1$ represents that a desired conformity to be controlled between the region covered by the prescription dose and the target region is 1. $f_{C1}$=TV_RI×TV_RI/(V_RI×TV), where TV_RI represents a volume of the intersection region between the region covered by the prescription dose and the target region, V_RI represents a volume of the region covered by the prescription dose, and TV represents a volume of the target region. The off-target dose control strategy $f_2$ may be expressed as $f_2=\omega_2\times\Sigma(\max(D_i-D_{i,pre}, 0))^2$, where $\omega_2$ is a preset parameter $D_i$ represents a dose corresponding to the i-th voxel to be optimized in the image, and $D_{i,pre}$ represents a dose corresponding to the i-th voxel in the predicted dose distribution. A first dose-calculating function obtained based on the conformance control strategy and the off-target dose control strategy and the initial dose-calculating function can be expressed as: $F_1=f_1+f_2$. The first dose distribution is obtained by computing (namely optimizing) the first dose-calculating function. The initial dose-calculating function, the control strategies and the first dose-calculating function described above may be presented in other forms.

Figure 8:
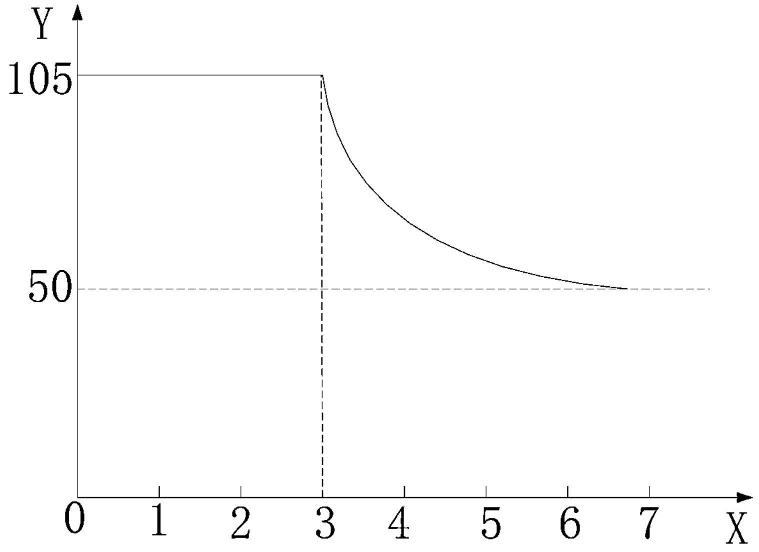
FIG. 8 is a view showing a control strategy for a target-region dose according to an embodiment of the present application.

In an embodiment, the off-target dose control strategy may be used to optimize the off-target dose according to a preset drop rule. The preset drop rule is shown in FIG. 8. In FIG. 8, the X-axis represents the shortest distance from a point in the off-target region to the target region boundary, and the Y-axis represents a dose.

In Step 710, a second dose-calculating function is obtained based on the first dose distribution and the target region dose control strategy, and the second dose-calculating function is optimized to obtain a second dose distribution.

After the computer equipment obtains the first dose distribution, the first dose distribution is optimized by using the target region dose control strategy to obtain the second dose distribution.

In an embodiment, the target dose control strategy $f_3$ may be expressed as: $f_3=\omega_3\times\Sigma(\min(D_i-D_{prescription}, 0))^2$, where $\omega_3$ is a pre-set parameter, $D_i$ represents a dose corresponding to the i-th voxel to be optimized in the image, and $D_{prescription}$ represents a prescription dose. The second dose-calculating function obtained based on the target dose control strategy may be expressed as: $F_2=f_3$, and the second dose distribution is obtained by computing (namely optimizing) the second dose-calculating function.

In Step 720, a third dose-calculating function is obtained based on the second dose distribution, the priority control strategy and the hot spot control strategy, and the third dose-calculating function is optimized to obtain a third dose distribution.

When the computer equipment obtains the second dose distribution, the dose distribution may be optimized by using the priority control strategy and the hot spot control strategy simultaneously to obtain the third dose distribution. In some embodiments of the present disclosure, the dose distribution may be firstly optimized by using the priority control strategy, and then optimized by using the hot spot control strategy to obtain the third dose distribution. Alternatively, the dose distribution may be firstly optimized by using the hot spot control strategy, and then optimized by using the priority control strategy to obtain the third dose distribution.

In an embodiment, the priority control strategy L may be expressed as:

$$L=\beta\cdot F+\langle\lambda, h_j\rangle+\alpha/2\cdot h_j^2,$$

where λ, α, β are all manually set parameters, F denotes an initial dose distribution when the dose distribution is to be optimized by using the priority control strategy L, and in this embodiment of the present application, for example, F denotes the second dose distribution. $h_j$ represents the dose distribution of the organ-at-risk region with a high priority in the dose distribution to be optimized, and the dose distribution of the organ-at-risk region with the high priority in the second dose-calculating function is optimized by using the Lagrange multiplier method. The hot spot control strategy $f_4$ may be expressed as:

$$f_4=N\times\omega_4\times\left[\left(\frac{1}{N}\sum_{i=1}^{N}(D_i-D_0)^p\right)^{\frac{1}{p}}\right]^2,$$

where $\omega_4$ is a manually set parameter, N represents the total number of voxels in the target region and outside the target region in the image, $D_0$ represents the maximum tolerable irradiated dose of all voxels set by the user, $D_i$ represents a dose corresponding to the i-th voxel to be optimized in the image, and p represents a parameter factor for the set dose volume effect in the target region and outside the target region. The third dose-calculating function obtained based on the priority control strategy and the hot spot control strategy may be expressed as $$F_3=\beta\cdot F+\langle\lambda, h_j\rangle+\frac{\alpha}{2}\cdot h_j^2+f_4,$$

and the third dose-calculating function is computed (namely optimized) to obtain the third dose distribution.

In Step 730, an objective dose-calculating function is obtained based on the third dose distribution and the uniformity control strategy, and the objective dose-calculating function is optimized to obtain an optimized dose distribution, and the optimized dose distribution is processed by using the automatic normalization control strategy to obtain the objective dose distribution.

After the computer equipment obtains the third dose distribution, the objective dose-calculating function is obtained based on the uniformity control strategy, and the objective dose-calculating function is optimized to obtain the optimized dose distribution, and the optimized dose distribution is processed by using the automatic normalization control strategy to obtain the objective dose distribution.

In an embodiment, the uniformity control strategy $f_5$ may be expressed as: $f_5=\omega_5\times[(D_2-D_{mean})^2+(D_{mean}-D_{9s})^2]$, where $\omega_5$ is a manually set parameter, $D_{mean}$ represents an average dose in the target region, $D_2$ represents a voxel dose corresponding to the first 2% of the voxel points after the voxel doses of the target region in the third dose distribution are sorted from high to low, and $D_{98}$ represents the voxel dose corresponding to the first 98% of the voxel points after the voxel doses of the target region in the third dose distribution are sorted from high to low. The average dose in the target region is updated according to the iteration calculation of the objective dose-calculating function corresponding to the objective dose distribution. In other words, the objective dose-calculating function constructed based on the uniformity control strategy is optimized iteratively until the number of iterations reaches a preset number, and the average dose in the target region is updated after each iteration. The objective dose-calculating function may be expressed as $F_4=f_5$. The objective dose-calculating function is optimized to obtain the optimized dose distribution. A normalization process is performed on the optimized dose distribution in the target region by using the automatic normalization control strategy according to a preset proportional coefficient. The automatic normalization control strategy may be expressed as $\gamma f_t$, where γ represents the preset proportional coefficient, and $f_t$ represents the optimized dose distribution in the target region. For example, assuming that after being optimized by the uniformity control strategy, the dose in the target region is 4980 cGy, and the prescription dose is 5000 cGy, then the proportionality coefficient may be expressed as 5000 cGy/4980 cGy.

In this embodiment, the priority control strategy, the off-target dose control strategy, the conformance control strategy, the hot spot control strategy, the target region dose control strategy, the uniformity control strategy and the automatic normalization control strategy in the plan-quality control strategy are used to optimize the dose distribution in stages, so that the obtained objective dose distribution is more accurate, and that the objective radiation delivery plan obtained using the objective dose distribution is more accurate. In addition, the dose-calculating functions and the control strategies, etc. described in this embodiment may be presented in other forms.

Figure 9:
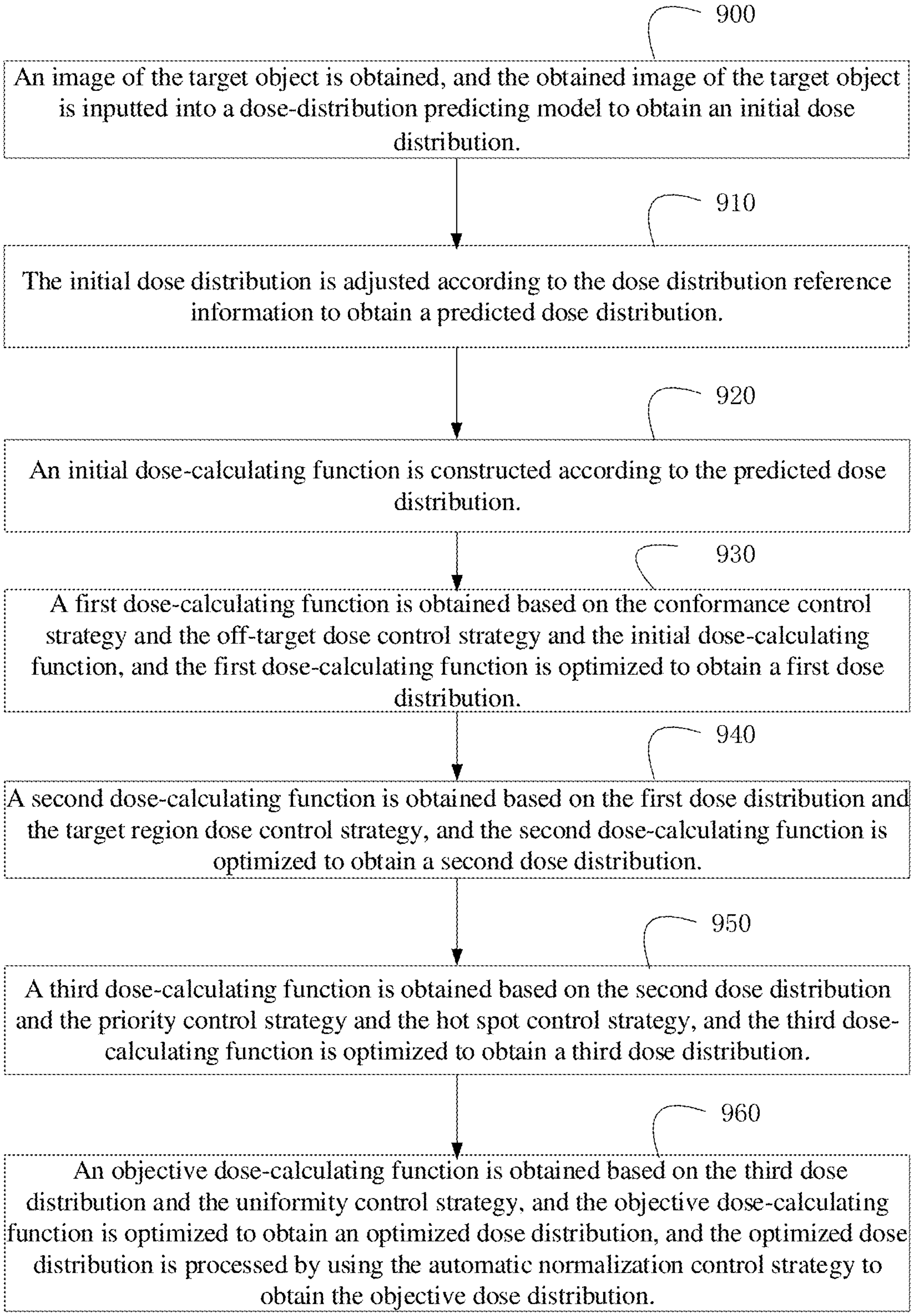
FIG. 9 is a schematic flow chart of steps of the method for determining the radiation delivery plan according to yet another embodiment of the present application.

Referring to FIG. 9, an embodiment of the present application provides a method for determining a radiation delivery plan, the method includes step 900 to step 970.

In Step 900, an image of the target object is obtained, and the obtained image of the target object is inputted into a dose-distribution predicting model to obtain an initial dose distribution.

In Step 910, the initial dose distribution is adjusted according to the dose distribution reference information to obtain a predicted dose distribution. The dose distribution parameter information includes at least one of a target dose of the target region in the image, a dose limit of the organ-at-risk region in the image, or a priority of the organ-at-risk region.

The dose distribution reference information may include a target table including priorities, and the predicted dose distribution obtained by adjusting the initial dose distribution according to the target table may be referred to as a clinical target. Alternatively, or additionally, the dose distribution reference information may also include other types of information, such as other types of target tables, fluence maps, etc. After the clinical target is generated, the target region and the organ-at-risk region in the image of the target object is contoured (i.e., the auxiliary structure is preprocessed) according to the clinical target and the initial dose distribution to distinguish the target region from the region outside the target region in the image.

In Step 920, an initial dose-calculating function is constructed according to the predicted dose distribution.

In Step 930, a first dose-calculating function is obtained based on the conformance control strategy and the off-target dose control strategy and the initial dose-calculating function, and the first dose-calculating function is optimized to obtain a first dose distribution.

In Step 940, a second dose-calculating function is obtained based on the first dose distribution and the target region dose control strategy, and the second dose-calculating function is optimized to obtain a second dose distribution.

In Step 950, a third dose-calculating function is obtained based on the second dose distribution and the priority control strategy and the hot spot control strategy, and the third dose-calculating function is optimized to obtain a third dose distribution.

In Step 960, an objective dose-calculating function is obtained based on the third dose distribution and the uniformity control strategy, and the objective dose-calculating function is optimized to obtain an optimized dose distribution, and the optimized dose distribution is processed by using the automatic normalization control strategy to obtain the objective dose distribution.

The present application further provides a method for determining a radiation delivery plan, and the method includes: obtaining an image of a target object; determining an initial dose distribution based on the image of the target object; determining a predicted dose distribution of the target object by adjusting the initial dose distribution according to dose distribution reference information; and determining an objective radiation delivery plan based on the predicted dose distribution.

In one of the embodiments, the dose distribution reference information comprises at least one of an objective dose of the target region in the image, a dose limit of the organ-at-risk region in the image, or a priority of the organ-at-risk region.

In one of the embodiments, determining the initial dose distribution based on the image of the target object includes: inputting the image of the target object into a dose-distribution predicting model to obtain the initial dose distribution.

In one of the embodiments, the target object includes a target region and an organ-at-risk region. The priority of the organ-at-risk region comprises a high priority, a medium priority, and a low priority.

Determining the predicted dose distribution of the target object by adjusting the initial dose distribution according to the dose distribution reference information comprises: selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

In one of the embodiments, determining the objective radiation delivery plan based on the predicted dose distribution, comprising: determining an objective dose distribution for the radiation delivery plan based on the predicted dose distribution and a plan-quality control strategy; and determining the objective radiation delivery plan based on the objective dose distribution.

In one of the embodiments, the plan-quality control strategy comprises different control strategies of a priority control strategy, an off-target dose control strategy, a conformance control strategy, a hot spot control strategy, a target region dose control strategy, a uniformity control strategy, and an automatic normalization control strategy; and determining the objective dose distribution for the radiation delivery plan based on the predicted dose distribution and the plan-quality control strategy comprises: determining the objective dose distribution for the radiation delivery plan by stages, based on one of or a combination from the different control strategies and the predicted dose distribution per stage.

It should be understood that, although the various steps in the flowcharts involved in the above-mentioned embodiments are displayed in sequence according to the indication of the arrows, these steps are not necessarily executed in sequence according to the order indicated by the arrows. Unless there is a clear explanation in this disclosure, the execution of these steps is not limited according to a strict order restriction, and these steps may be executed in other orders. Moreover, at least part of the steps in the flowcharts involved in the above-mentioned embodiments may include multiple steps or multiple stages, and these steps or stages are not necessarily executed at the same time, but may be executed at different time, and these steps or stages are not necessarily executed in sequence, but may be executed in turn or alternately with other steps or with at least part of the steps or stages in other steps.

Based on the same or similar inventive concept, the embodiments of the present application also provide a device for determining a radiation delivery plan for implementing the above-mentioned method for determining the radiation delivery plan. The solutions implemented for solving the problem provided by the device are similar to the solutions for implementing the above-mentioned method, so the specific limitations in the embodiments of one or more devices for determining the radiation delivery plan provided hereinafter may refer to the limitations of the method for determining the radiation delivery plan above, and will not be described repeatedly herein.

Figure 10:
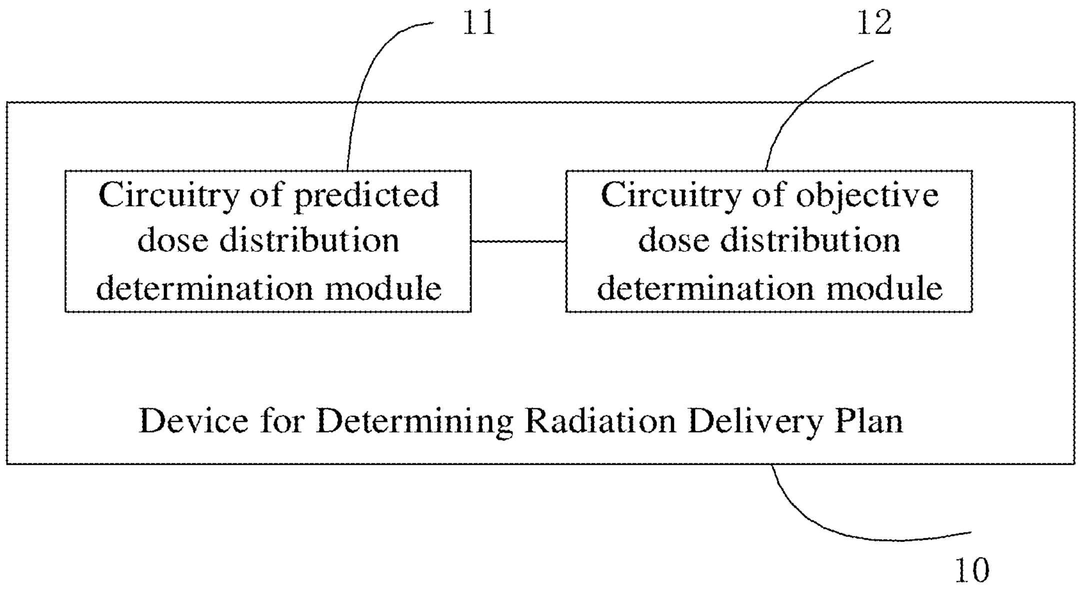
FIG. 10 is a view showing a structure of a device for determining a radiation delivery plan according to an embodiment of the present application.

In an embodiment, as shown in FIG. 10, a device for determining a radiation delivery plan 10 is provided, and includes: circuitry of a predicted dose distribution determination module 11 and circuitry of an objective dose distribution determination module 12.

The circuitry of the predicted dose distribution determination module 11 is configured to obtain an image of a target object, and determine a predicted dose distribution of the target object according to the image of the target object.

The circuitry of the objective dose distribution determination module 12 is configured to determine an objective dose distribution for a radiation delivery plan based on the predicted dose distribution and a plan-quality control strategy.

In an embodiment, the plan-quality control strategy may include at least one of a priority control strategy, an off-target dose control strategy, a conformance control strategy, a hot spot control strategy, a target region dose control strategy, a uniformity control strategy, or an automatic normalization control strategy.

In an embodiment, the circuitry of the objective dose distribution determination module 12 is specifically configured to: select any control strategy from the plan-quality control strategy as a current control strategy, optimize a current dose distribution according to the current control strategy to obtain an optimized dose distribution; use the optimized dose distribution as an updated current dose distribution, and use any remaining control strategy in the plan-quality control strategy as an updated current control strategy, return to execute the step of optimizing the current dose distribution according to the current control strategy to obtain the optimized dose distribution until all control strategies of the plan-quality control strategy are traversed, and use the optimized dose distribution obtained finally as the objective dose distribution.

In an embodiment, the circuitry of the predicted dose distribution acquisition module 11 is specifically configured to obtain the image of the target object, input the image of the target object into a dose-distribution predicting model, and obtain the predicted dose distribution.

In an embodiment, the circuitry of the predicted dose distribution acquisition module 11 is specifically configured to obtain the image of the target object and input the image into the dose-distribution predicting model to obtain an initial dose distribution. The dose distribution reference information includes at least one of an objective dose of a target region in the image, a dose limit of an organ-at-risk region in the image, or a priority of the organ-at-risk region.

In an embodiment, the circuitry of the objective dose distribution determination module 12 is specifically configured to: obtain a first dose-calculating function based on the conformance control strategy and the off-target dose control strategy and the predicted dose distribution, and optimize the first dose-calculating function to obtain a first dose distribution; obtain a second dose-calculating function based on the first dose distribution and the target region dose control strategy, and optimize the second dose-calculating function to obtain a second dose distribution; obtain a third dose-calculating function based on the second dose distribution and the priority control strategy and the hot spot control strategy, and optimize the third dose-calculating function obtain a third dose distribution; obtain an objective dose-calculating function based on the third dose distribution and the uniformity control strategy, and optimize the objective dose-calculating function to obtain an optimized dose distribution, and process the optimized dose distribution by using the automatic normalization control strategy to obtain the objective dose distribution.

The circuitries in the above-mentioned device for determining radiation delivery plan may be partially implemented by software, hardware and a combination thereof. Each circuitry of module may be embedded in or independent of a processor in a computer equipment in a form of hardware, so that the processor calls and executes operations corresponding to each circuitry of module above.

In an embodiment, a computer equipment is provided. The computer equipment may be a terminal, and an internal structure thereof may be shown in FIG. 1. Those skilled in the art may understand that the structure shown in FIG. 1 is only a block diagram of part of the structure related to the solution of the present application, and does not constitute a limitation on the computer equipment to which the solution of the present application is applied. The specific computer equipment may include more or fewer components than those shown in the figure, or may combine certain components, or may have a different arrangement of components.

In an embodiment, a computer equipment is provided, and includes a memory and a processor. A computer program is stored in the memory, and the processor, when performing the computer program, performs the following steps: obtaining an image of a target object, and determining a predicted dose distribution of the target object according to the image of the target object; and determining an objective dose distribution for a radiation delivery plan based on the predicted dose distribution and a plan-quality control strategy.

In an embodiment, the plan-quality control strategy includes at least one of a priority control strategy, an off-target dose control strategy, a conformance control strategy, a hot spot control strategy, a target region dose control strategy, a uniformity control strategy, or an automatic normalization control strategy.

In an embodiment, the processor, when executing the computer program, performs the following steps: selecting any control strategy from the plan-quality control strategy as a current control strategy, and optimizing a current dose distribution according to the current control strategy to obtain an optimized dose distribution; using the optimized dose distribution as an updated current dose distribution, and using any remaining control strategy in the plan-quality control strategy as an updated current control strategy, returning to execute the step of optimizing the current dose distribution according to the current control strategy to obtain the optimized dose distribution until all control strategies of the plan-quality control strategy are traversed, and using the optimized dose distribution obtained finally as the objective dose distribution.

In an embodiment, the processor, when executing the computer program, performs the following steps: obtaining the image of the target object, inputting the image of the target object into a dose-distribution predicting model, and obtaining the predicted dose distribution.

In an embodiment, the processor, when executing the computer program, performs the following steps: obtaining the image of the target object and inputting the image into the dose-distribution predicting model to obtain an initial dose distribution; and adjusting the initial dose distribution according to dose distribution reference information to obtain the predicted dose distribution. The dose distribution reference information includes at least one of an objective dose of a target region in the image, a dose limit of an organ-at-risk region in the image, or a priority of the organ-at-risk region.

In an embodiment, the processor, when executing the computer program, performs the following steps: obtaining a first dose-calculating function based on the conformance control strategy and the off-target dose control strategy and the predicted dose distribution, and optimizing the first dose-calculating function to obtain a first dose distribution; obtaining a second dose-calculating function based on the first dose distribution and the target region dose control strategy, and optimizing the second dose-calculating function to obtain a second dose distribution; obtaining a third dose-calculating function based on the second dose distribution and the priority control strategy and the hot spot control strategy, and optimizing the third dose-calculating function obtain a third dose distribution; obtaining an objective dose-calculating function based on the third dose distribution and the uniformity control strategy, and optimizing the objective dose-calculating function to obtain an optimized dose distribution, and processing the optimized dose distribution by using the automatic normalization control strategy to obtain the objective dose distribution.

In an embodiment, a non-transitory computer-readable storage medium is provided, and computer-executable instructions are stored on the storage medium. The computer-executable instructions, when executed by a processor, perform the following steps: obtaining an image of a target object, and determining a predicted dose distribution of the target object according to the image of the target object; and determining an objective dose distribution for a radiation delivery plan based on the predicted dose distribution and a plan-quality control strategy.

In an embodiment, the plan-quality control strategy includes at least one of a priority control strategy, an off-target dose control strategy, a conformance control strategy, a hot spot control strategy, a target region dose control strategy, a uniformity control strategy, or an automatic normalization control strategy.

In an embodiment, the computer-executable instructions, when executed by a processor, perform the following steps: selecting any control strategy from the plan-quality control strategy as a current control strategy, and optimizing a current dose distribution according to the current control strategy to obtain an optimized dose distribution; using the optimized dose distribution as an updated current dose distribution, and using any remaining control strategy in the plan-quality control strategy as an updated current control strategy, returning to execute the step of optimizing the current dose distribution according to the current control strategy to obtain the optimized dose distribution until all control strategies of the plan-quality control strategy are traversed, and using the optimized dose distribution obtained finally as the objective dose distribution.

In an embodiment, the computer-executable instructions, when executed by a processor, perform the following steps: obtaining the image of the target object, inputting the image of the target object into a dose-distribution predicting model, and obtaining the predicted dose distribution.

In an embodiment, the computer-executable instructions, when executed by a processor, perform the following steps: obtaining the image of the target object and inputting the image into the dose-distribution predicting model to obtain an initial dose distribution; and adjusting the initial dose distribution according to dose distribution reference information to obtain the predicted dose distribution. The dose distribution reference information includes at least one of an objective dose of a target region in the image, a dose limit of an organ-at-risk region in the image, or a priority of the organ-at-risk region.

In an embodiment, the computer-executable instructions, when executed by a processor, perform the following steps: obtaining a first dose-calculating function based on the conformance control strategy and the off-target dose control strategy and the predicted dose distribution, and optimizing the first dose-calculating function to obtain a first dose distribution; obtaining a second dose-calculating function based on the first dose distribution and the target region dose control strategy, and optimizing the second dose-calculating function to obtain a second dose distribution; obtaining a third dose-calculating function based on the second dose distribution and the priority control strategy and the hot spot control strategy, and optimizing the third dose-calculating function obtain a third dose distribution; obtaining an objective dose-calculating function based on the third dose distribution and the uniformity control strategy, and optimizing the objective dose-calculating function to obtain an optimized dose distribution, and processing the optimized dose distribution by using the automatic normalization control strategy to obtain the objective dose distribution.

In an embodiment, a computer program product is provided, and includes a computer program. The computer program, when executed by a processor, performs the following steps: obtaining an image of a target object, and determining a predicted dose distribution of the target object according to the image of the target object; and determining an objective dose distribution for a radiation delivery plan based on the predicted dose distribution and a plan-quality control strategy.

In an embodiment, the plan-quality control strategy includes at least one of a priority control strategy, an off-target dose control strategy, a conformance control strategy, a hot spot control strategy, a target region dose control strategy, a uniformity control strategy, or an automatic normalization control strategy.

In an embodiment, the computer program, when executed by a processor, performs the following steps: selecting any control strategy from the plan-quality control strategy as a current control strategy, and optimizing a current dose distribution according to the current control strategy to obtain an optimized dose distribution; using the optimized dose distribution as an updated current dose distribution, and using any remaining control strategy in the plan-quality control strategy as an updated current control strategy, returning to execute the step of optimizing the current dose distribution according to the current control strategy to obtain the optimized dose distribution until all control strategies of the plan-quality control strategy are traversed, and using the optimized dose distribution obtained finally as the objective dose distribution.

In an embodiment, the computer program, when executed by a processor, performs the following steps: obtaining the image of the target object, inputting the image of the target object into a dose-distribution predicting model, and obtaining the predicted dose distribution.

In an embodiment, the computer program, when executed by a processor, performs the following steps: obtaining the image of the target object and inputting the image into the dose-distribution predicting model to obtain an initial dose distribution; and adjusting the initial dose distribution according to dose distribution reference information to obtain the predicted dose distribution. The dose distribution reference information includes at least one of an objective dose of a target region in the image, a dose limit of an organ-at-risk region in the image, or a priority of the organ-at-risk region.

In an embodiment, the computer program, when executed by a processor, performs the following steps: obtaining a first dose-calculating function based on the conformance control strategy and the off-target dose control strategy and the predicted dose distribution, and optimizing the first dose-calculating function to obtain a first dose distribution; obtaining a second dose-calculating function based on the first dose distribution and the target region dose control strategy, and optimizing the second dose-calculating function to obtain a second dose distribution; obtaining a third dose-calculating function based on the second dose distribution and the priority control strategy and the hot spot control strategy, and optimizing the third dose-calculating function obtain a third dose distribution; obtaining an objective dose-calculating function based on the third dose distribution and the uniformity control strategy, and optimizing the objective dose-calculating function to obtain an optimized dose distribution, and processing the optimized dose distribution by using the automatic normalization control strategy to obtain the objective dose distribution.

Those ordinary skilled in the art may understand that all or part of the process in the method of the above embodiments may be implemented by instructing the relevant hardware through executable instructions, and the executable instructions may be stored in a non-transitory computer-readable storage medium. The executable instructions, when being executed, may include the processes of the embodiments of the methods above. Where, any reference to memory, storage, database, or other medium used in the various embodiments provided in this application may include at least one of non-transitory and transitory memory. Non-transitory memory may include read-only memory (ROM), magnetic tape, floppy disk, flash memory, or optical memory, high-density embedded non-transitory memory, resistance random access memory (ReRAM), magneto resistive random-access memory (MRAM), ferroelectric random-access memory (FRAM), phase change memory (PCM), graphene memory, and the like. The transitory memory may include random access memory (RAM) or external cache memory. By way of illustration and not limitation, the RAM may be in various forms, such as static random-access memory (SRAM) or dynamic random-access memory (DRAM), etc. The databases involved in the embodiments provided in the present application may include at least one of a relational database and a non-relational database. The non-relational databases may include, but are not limited to, a blockchain-based distributed database, and the like. The processors involved in the embodiments provided in the present application may be, but are not limited to, a general-purpose processor, a central processing unit, a graphics processor, a digital signal processor, a programmable logic, a quantum-computing-based data processing logic, and the like.

The technical features of the embodiments above may be combined arbitrarily. To make the description concise, not all possible combinations of the technical features in the above embodiments are described. However, as long as there are no contradictions in the combinations of these technical features, all of the combinations should be considered to be within the scope of the specification.

The embodiments above only represent several implementation modes of the present application, and the description thereof is relatively specific and detailed, but it should not be construed as limiting the scope of the patent. It should be noted that for those skilled in the art, various modifications and improvements may be made without departing from the concept of the present application, and all these modifications and improvements belong to the protection scope of the present application. Therefore, the scope of protection of the patent application should be subject to the appended claims.

What is claimed is:

1. A method for determining a radiation delivery plan, comprising:

obtaining an image of a target object, and determining a predicted dose distribution of the target object according to the image of the target object; and determining an objective dose distribution for the radiation delivery plan based on the predicted dose distribution and a plan-quality control strategy used for optimizing a dose distribution and comprising different control strategies.

2. The method of claim 1, wherein:

determining the objective dose distribution for the radiation delivery plan based on the predicted dose distribution and the plan-quality control strategy comprises: determining the objective dose distribution for the radiation delivery plan by stages, based on one of or a combination from the different control strategies and the predicted dose distribution per stage.

3. The method of claim 2, wherein the different control strategies comprise the priority control strategy, the off-target dose control strategy, the conformance control strategy, the hot spot control strategy, the target region dose control strategy, the uniformity control strategy, and the automatic normalization control strategy; and determining the objective dose distribution for the radiation delivery plan by stages, based on one of or the combination from the different control strategies and the predicted dose distribution comprises:

obtaining a first dose-calculating function based on the conformance control strategy, the off-target dose control strategy and the predicted dose distribution, and optimizing the first dose-calculating function to obtain a first dose distribution;

obtaining a second dose-calculating function based on the first dose distribution and the target region dose control strategy, and optimizing the second dose-calculating function to obtain a second dose distribution;

obtaining a third dose-calculating function based on the second dose distribution, the priority control strategy and the hot spot control strategy, and optimizing the third dose-calculating function to obtain a third dose distribution; and obtaining an objective dose-calculating function based on the third dose distribution and the uniformity control strategy, optimizing the objective dose-calculating function to obtain an optimized dose distribution, and processing the optimized dose distribution by using the automatic normalization control strategy to obtain the objective dose distribution.

4. The method of claim 1, wherein the plan-quality control strategy comprises at least one of:

a priority control strategy, an off-target dose control strategy, a conformance control strategy, a hot spot control strategy, a target region dose control strategy, a uniformity control strategy, or an automatic normalization control strategy.

5. The method of claim 1, wherein, determining the objective dose distribution for the radiation delivery plan based on the predicted dose distribution and the plan-quality control strategy, comprises:

constructing an initial dose-calculating function based on the predicted dose distribution;

obtaining an objective dose-calculating function based on the initial dose-calculating function and the plan-quality control strategy; and computing the objective dose-calculating function to obtain the objective dose distribution.

6. The method of claim 1, wherein, determining the objective dose distribution for the radiation delivery plan based on the predicted dose distribution and the plan-quality control strategy, comprises:

selecting any control strategy from the plan-quality control strategy as a current control strategy;

optimizing a current dose distribution according to the current control strategy to obtain an optimized dose distribution; and using the optimized dose distribution as an updated current dose distribution, and using any remaining control strategy in the plan-quality control strategy as an updated current control strategy, returning to execute the step of optimizing the current dose distribution according to the current control strategy to obtain the optimized dose distribution, until all control strategies of the plan-quality control strategy are traversed, and using the optimized dose distribution obtained finally as the objective dose distribution.

7. The method of claim 1, wherein obtaining the image of the target object and determining the predicted dose distribution of the target object according to the image of the target object comprises:

obtaining the image of the target object, inputting the image of the target object into a dose-distribution predicting model to obtain the predicted dose distribution.

8. The method of claim 7, wherein obtaining the image of the target object, and inputting the image of the target object into a dose-distribution predicting model to obtain the predicted dose distribution, comprise:

obtaining the image of the target object, and inputting the image of the target object into the dose-distribution predicting model to obtain an initial dose distribution; and adjusting the initial dose distribution according to dose distribution reference information to obtain the predicted dose distribution, wherein the dose distribution reference information comprises at least one of an objective dose of a target region in the image, a dose limit of an organ-at-risk region in the image, or a priority of the organ-at-risk region.

9. The method of claim 8, wherein:

the objective dose of the target region in the image refers to a prescription dose set for the target region in the image according to specificity of the image;

the dose limit of the organ-at-risk region in the image refers to a lower limit of unacceptable dose set for the organ-at-risk region outside the target in the image; and the priority of the organ-at-risk region refers to the priority of the organ-at-risk region relative to the target region.

10. The method of claim 9, wherein:

the priority of the organ-at-risk region comprises a high priority, a medium priority, and a low priority; and adjusting the initial dose distribution according to dose distribution reference information to obtain the predicted dose distribution, comprising:

selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

11. The method of claim 7, wherein before inputting the image of the target object into the dose-distribution predicting model to obtain the predicted dose distribution, the method further comprises:

obtaining a training sample image set, contouring a target region in the training sample image set, and obtaining gold standard dose information of a dose distribution in the target region and outside the target region; and inputting the contoured training sample image set and the gold standard dose information into an initial neural network, and performing an iterative training according to a preset loss function, until a preset iteration condition is met to obtain the dose-distribution predicting model.

12. A computer equipment, comprising a memory and a processor, wherein the memory having a computer program stored thereon, and the processor, when executing the computer program, performs steps of the method of claim 1.

13. A non-transitory computer-readable storage medium, having computer-executable instructions stored thereon, wherein the computer-executable instructions, when executed by a processor, perform steps of the method of claim 1.

14. A method for determining a radiation delivery plan, comprising:

obtaining an image of a target object, comprising a target region and an organ-at-risk region; a priority of the organ-at-risk region comprising a high priority, a medium priority, and a low priority;

determining an initial dose distribution based on the image of the target object;

determining a predicted dose distribution of the target object by adjusting the initial dose distribution according to dose distribution reference information, the dose distribution reference information comprising at least one of an objective dose of the target region in the image, a dose limit of the organ-at-risk region in the image, or the priority of the organ-at-risk region; and determining an objective radiation delivery plan based on the predicted dose distribution;

wherein determining the predicted dose distribution of the target object by adjusting the initial dose distribution according to the dose distribution reference information comprises:

selecting the minimum value between the dose limit of the organ-at-risk region and the initial dose distribution to be the predicted dose distribution of the organ-at-risk region with the high priority; and determining the predicted dose distribution of the organ-at-risk region with the medium priority or the low priority according to the initial dose distribution.

15. The method of claim 14, wherein determining the initial dose distribution based on the image of the target object comprises: inputting the image of the target object into a dose-distribution predicting model to obtain the initial dose distribution.

16. The method of claim 14, wherein determining the objective radiation delivery plan based on the predicted dose distribution, comprising:

determining an objective dose distribution for the radiation delivery plan based on the predicted dose distribution and a plan-quality control strategy; and determining the objective radiation delivery plan based on the objective dose distribution.

17. The method of claim 16, wherein:

the plan-quality control strategy comprises different control strategies of a priority control strategy, an off-target dose control strategy, a conformance control strategy, a hot spot control strategy, a target region dose control strategy, a uniformity control strategy, and an automatic normalization control strategy; and determining the objective dose distribution for the radiation delivery plan based on the predicted dose distribution and the plan-quality control strategy comprises: determining the objective dose distribution for the radiation delivery plan by stages, based on one of or a combination from the different control strategies and the predicted dose distribution per stage.

* * * * *